United States Patent
McNall, III et al.

(10) Patent No.: US 8,979,842 B2
(45) Date of Patent: Mar. 17, 2015

(54) WIRE ELECTRODE DEVICES FOR TONSILLECTOMY AND ADENOIDECTOMY

(75) Inventors: Ralph I. McNall, III, Menlo Park, CA (US); Kay W. Chang, Menlo Park, CA (US); Paul O. Davison, Montara, CA (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 368 days.

(21) Appl. No.: 13/488,213

(22) Filed: Jun. 4, 2012

(65) Prior Publication Data

US 2012/0330311 A1     Dec. 27, 2012

Related U.S. Application Data

(60) Provisional application No. 61/495,853, filed on Jun. 10, 2011.

(51) Int. Cl.
*A61B 18/18* (2006.01)
*A61B 18/14* (2006.01)
(Continued)

(52) U.S. Cl.
CPC ........... *A61B 18/1485* (2013.01); *A61B 18/149* (2013.01); *A61B 2018/00083* (2013.01); *A61B 2018/00327* (2013.01); *A61B 2018/00601* (2013.01); *A61B 2218/007* (2013.01); *A61B 2017/00323* (2013.01); *A61B 2018/00589* (2013.01); *A61B 2018/144* (2013.01); *A61B 2018/1495* (2013.01)
USPC .......................................................... 606/46

(58) Field of Classification Search
CPC ........ A61B 18/00; A61B 18/12; A61B 18/18; A61B 18/1815; A61B 2018/18; A61B 2018/1815; A61N 5/00; A61N 5/02; A61N 5/022; A61N 2005/0643
USPC ............................................................ 606/46
See application file for complete search history.

(56) References Cited

U.S. PATENT DOCUMENTS

| | | |
|---|---|---|
| 3,799,168 A | 3/1974 | Peters |
| 3,903,891 A | 9/1975 | Brayshaw |
| 3,970,088 A | 7/1976 | Morrison |

(Continued)

FOREIGN PATENT DOCUMENTS

| | | |
|---|---|---|
| EP | 0 012 037 A1 | 6/1980 |
| EP | 0 517 244 A1 | 12/1992 |

(Continued)

OTHER PUBLICATIONS

Cushing, H. (Dec. 1928). "Electro-Surgery as an Aid to the Removal of Intracranial Tumors," *Surgery, Gynecology and Obstetrics*, XLVII(6):751-784.

(Continued)

*Primary Examiner* — Robert N Wieland
(74) *Attorney, Agent, or Firm* — Jeffrey J. Hohenshell

(57) ABSTRACT

Monopolar electrosurgery devices adapted for resecting tonsil and adenoid tissue. The devices minimize thermal injury by employing a plasma generated by pulsed electrical signals to precisely and effectively cut or coagulate the tissues. Suction may also be applied to the tissues to enhance the cutting, coagulation, and tissue manipulation functions. The devices include an interchangeable tip that may be switched for another tip, depending on which tip may be more suitable for tonsillectomy or adenoidectomy.

22 Claims, 8 Drawing Sheets

(51) Int. Cl.
*A61B 18/00* (2006.01)
*A61B 17/00* (2006.01)

(56) References Cited

U.S. PATENT DOCUMENTS

| | | | |
|---|---|---|---|
| 3,987,795 A | 10/1976 | Morrison | |
| 4,034,762 A | 7/1977 | Cosens et al. | |
| 4,043,342 A | 8/1977 | Morrison, Jr. | |
| 4,074,718 A | 2/1978 | Morrison, Jr. | |
| 4,161,950 A | 7/1979 | Doss et al. | |
| 4,202,337 A | 5/1980 | Hren et al. | |
| 4,211,230 A | 7/1980 | Woltosz | |
| 4,228,800 A | 10/1980 | Degler, Jr. et al. | |
| 4,248,231 A | 2/1981 | Herczog et al. | |
| 4,429,694 A | 2/1984 | McGreevy | |
| 4,438,766 A | 3/1984 | Bowers | |
| 4,473,075 A | 9/1984 | Rexroth | |
| 4,476,862 A | 10/1984 | Pao | |
| 4,492,231 A | 1/1985 | Auth | |
| 4,534,347 A | 8/1985 | Taylor | |
| 4,559,943 A | 12/1985 | Bowers | |
| 4,589,411 A | 5/1986 | Friedman | |
| 4,590,934 A | 5/1986 | Malis et al. | |
| 4,593,691 A | 6/1986 | Lindstrom et al. | |
| 4,597,388 A | 7/1986 | Koziol et al. | |
| 4,655,215 A | 4/1987 | Pike | |
| 4,674,498 A | 6/1987 | Stasz | |
| 4,674,499 A | 6/1987 | Pao | |
| 4,682,596 A | 7/1987 | Bales et al. | |
| 4,781,175 A | 11/1988 | McGreevy et al. | |
| 4,805,616 A | 2/1989 | Pao | |
| 4,901,709 A | 2/1990 | Rattner | |
| 4,927,420 A | 5/1990 | Newkirk et al. | |
| 4,936,301 A | 6/1990 | Rexroth et al. | |
| 4,938,761 A | 7/1990 | Ensslin | |
| 4,943,290 A | 7/1990 | Rexroth et al. | |
| 5,080,660 A | 1/1992 | Buelna | |
| 5,088,997 A * | 2/1992 | Delahuerga et al. | 606/42 |
| 5,108,391 A | 4/1992 | Flachenecker et al. | |
| RE33,925 E | 5/1992 | Bales et al. | |
| 5,151,102 A | 9/1992 | Kamiyama et al. | |
| 5,217,457 A | 6/1993 | Delahuerga et al. | |
| 5,234,428 A * | 8/1993 | Kaufman | 606/45 |
| 5,254,121 A | 10/1993 | Manevitz et al. | |
| 5,267,994 A | 12/1993 | Gentelia et al. | |
| 5,267,998 A | 12/1993 | Hagen | |
| 5,281,216 A | 1/1994 | Klicek | |
| 5,300,068 A | 4/1994 | Rosar et al. | |
| 5,318,563 A | 6/1994 | Malis et al. | |
| 5,348,553 A | 9/1994 | Whitney | |
| 5,423,814 A | 6/1995 | Zhu et al. | |
| 5,454,809 A | 10/1995 | Janssen | |
| 5,472,443 A | 12/1995 | Cordis et al. | |
| 5,496,314 A | 3/1996 | Eggers | |
| 5,549,604 A | 8/1996 | Sutcu et al. | |
| 5,569,242 A | 10/1996 | Lax et al. | |
| 5,599,346 A | 2/1997 | Edwards et al. | |
| 5,647,871 A | 7/1997 | Levine et al. | |
| 5,658,279 A | 8/1997 | Nardella et al. | |
| 5,669,904 A | 9/1997 | Platt, Jr. et al. | |
| 5,683,366 A | 11/1997 | Eggers et al. | |
| 5,697,281 A | 12/1997 | Eggers et al. | |
| 5,697,536 A | 12/1997 | Eggers et al. | |
| 5,697,882 A | 12/1997 | Eggers et al. | |
| 5,697,909 A | 12/1997 | Eggers et al. | |
| 5,700,262 A | 12/1997 | Acosta et al. | |
| 5,766,153 A | 6/1998 | Eggers et al. | |
| 5,766,170 A | 6/1998 | Eggers | |
| 5,785,704 A | 7/1998 | Bille et al. | |
| 5,843,019 A | 12/1998 | Eggers et al. | |
| 5,860,976 A | 1/1999 | Billings et al. | |
| 5,873,855 A | 2/1999 | Eggers et al. | |
| 5,891,095 A | 4/1999 | Eggers et al. | |
| 5,891,142 A | 4/1999 | Eggers et al. | |
| 5,919,189 A | 7/1999 | Benderev | |
| 5,958,266 A | 9/1999 | Fugo et al. | |
| 5,971,980 A | 10/1999 | Sherman | |
| 6,004,319 A | 12/1999 | Goble et al. | |
| 6,032,674 A | 3/2000 | Eggers et al. | |
| 6,047,700 A | 4/2000 | Eggers et al. | |
| 6,053,172 A | 4/2000 | Hovda et al. | |
| 6,056,746 A | 5/2000 | Goble et al. | |
| 6,059,782 A | 5/2000 | Novak et al. | |
| 6,059,783 A | 5/2000 | Kirwan, Jr. | |
| 6,066,134 A | 5/2000 | Eggers et al. | |
| 6,066,137 A | 5/2000 | Greep | |
| 6,102,046 A | 8/2000 | Weinstein et al. | |
| 6,113,594 A | 9/2000 | Savage | |
| 6,117,109 A | 9/2000 | Eggers et al. | |
| 6,132,427 A | 10/2000 | Jones et al. | |
| 6,135,998 A | 10/2000 | Palanker | |
| 6,149,620 A | 11/2000 | Baker et al. | |
| 6,149,646 A | 11/2000 | West, Jr. et al. | |
| 6,165,175 A | 12/2000 | Wampler et al. | |
| 6,174,309 B1 | 1/2001 | Wrublewski et al. | |
| 6,183,469 B1 | 2/2001 | Thapliyal et al. | |
| 6,190,381 B1 | 2/2001 | Olsen et al. | |
| 6,210,404 B1 | 4/2001 | Shadduck | |
| 6,228,081 B1 | 5/2001 | Goble | |
| 6,228,082 B1 | 5/2001 | Baker et al. | |
| 6,228,084 B1 | 5/2001 | Kirwan, Jr. | |
| 6,241,724 B1 | 6/2001 | Fleischman et al. | |
| 6,254,600 B1 | 7/2001 | Willink et al. | |
| 6,267,757 B1 | 7/2001 | Aita et al. | |
| 6,287,305 B1 | 9/2001 | Heim et al. | |
| 6,287,306 B1 | 9/2001 | Kroll et al. | |
| 6,293,945 B1 | 9/2001 | Parins et al. | |
| 6,352,535 B1 | 3/2002 | Lewis et al. | |
| 6,355,032 B1 | 3/2002 | Hovda et al. | |
| 6,358,248 B1 | 3/2002 | Mulier et al. | |
| 6,364,877 B1 | 4/2002 | Goble et al. | |
| 6,398,779 B1 | 6/2002 | Buysse et al. | |
| 6,447,511 B1 | 9/2002 | Slater | |
| 6,458,121 B1 | 10/2002 | Rosenstock et al. | |
| 6,478,794 B1 | 11/2002 | Trapp et al. | |
| 6,479,785 B1 | 11/2002 | Fugo et al. | |
| 6,482,201 B1 | 11/2002 | Olsen et al. | |
| 6,482,205 B1 | 11/2002 | Bonnet | |
| 6,500,176 B1 | 12/2002 | Truckai et al. | |
| 6,530,924 B1 | 3/2003 | Ellman et al. | |
| 6,533,781 B2 | 3/2003 | Heim et al. | |
| 6,544,261 B2 | 4/2003 | Ellsberry et al. | |
| 6,589,237 B2 | 7/2003 | Woloszko et al. | |
| 6,620,157 B1 | 9/2003 | Dabney et al. | |
| 6,620,160 B2 | 9/2003 | Lewis et al. | |
| 6,679,269 B2 | 1/2004 | Swanson | |
| 6,726,683 B1 | 4/2004 | Shaw | |
| 6,749,608 B2 | 6/2004 | Garito et al. | |
| 6,770,071 B2 | 8/2004 | Woloszko et al. | |
| 6,780,178 B2 | 8/2004 | Palanker et al. | |
| 6,787,730 B2 | 9/2004 | Coccio et al. | |
| 6,802,842 B2 | 10/2004 | Ellman et al. | |
| 6,818,102 B1 | 11/2004 | Viol | |
| 6,837,887 B2 | 1/2005 | Woloszko et al. | |
| 6,942,662 B2 | 9/2005 | Goble et al. | |
| 6,949,096 B2 | 9/2005 | Davison et al. | |
| 6,960,204 B2 | 11/2005 | Eggers et al. | |
| 6,991,631 B2 | 1/2006 | Woloszko et al. | |
| 7,004,941 B2 | 2/2006 | Tvinnereim et al. | |
| 7,090,672 B2 | 8/2006 | Underwood et al. | |
| 7,094,215 B2 | 8/2006 | Davison et al. | |
| RE39,358 E | 10/2006 | Goble | |
| 7,115,139 B2 | 10/2006 | McClurken et al. | |
| 7,131,969 B1 | 11/2006 | Hovda et al. | |
| 7,169,143 B2 | 1/2007 | Eggers et al. | |
| 7,179,255 B2 | 2/2007 | Lettice et al. | |
| 7,182,762 B2 | 2/2007 | Bortkiewicz | |
| 7,186,234 B2 | 3/2007 | Dahla et al. | |
| 7,192,428 B2 | 3/2007 | Eggers et al. | |
| 7,195,627 B2 | 3/2007 | Amoah et al. | |
| 7,195,630 B2 | 3/2007 | Ciarrocca | |
| 7,201,750 B1 | 4/2007 | Eggers et al. | |
| 7,238,185 B2 | 7/2007 | Palanker et al. | |
| 7,270,658 B2 | 9/2007 | Woloszko et al. | |

(56) References Cited

U.S. PATENT DOCUMENTS

| | | |
|---|---|---|
| 7,270,661 B2 | 9/2007 | Dahla et al. |
| 7,276,063 B2 | 10/2007 | Davison et al. |
| 7,303,561 B2 | 12/2007 | Ouchi |
| 7,357,802 B2 | 4/2008 | Palanker et al. |
| 7,429,262 B2 | 9/2008 | Woloszko et al. |
| 7,435,247 B2 | 10/2008 | Woloszko et al. |
| 7,445,618 B2 | 11/2008 | Eggers et al. |
| 7,468,059 B2 | 12/2008 | Eggers et al. |
| 7,736,361 B2 | 6/2010 | Palanker et al. |
| 7,789,879 B2 | 9/2010 | Palanker et al. |
| 7,901,403 B2 | 3/2011 | Woloszko et al. |
| 8,043,286 B2 | 10/2011 | Palanker et al. |
| 8,137,345 B2 | 3/2012 | McNall, III et al. |
| 8,177,783 B2 | 5/2012 | Davison et al. |
| 8,632,537 B2 | 1/2014 | McNall, III et al. |
| 2001/0012934 A1 | 8/2001 | Chandrasekaran et al. |
| 2001/0025177 A1 | 9/2001 | Woloszko et al. |
| 2001/0034519 A1 | 10/2001 | Goble et al. |
| 2002/0026186 A1 | 2/2002 | Woloszko et al. |
| 2002/0052599 A1 | 5/2002 | Goble et al. |
| 2002/0052600 A1 | 5/2002 | Davison et al. |
| 2003/0069573 A1 | 4/2003 | Kadhiresan et al. |
| 2004/0024401 A1 | 2/2004 | Garito et al. |
| 2004/0049251 A1 | 3/2004 | Knowlton |
| 2004/0054366 A1 | 3/2004 | Davison et al. |
| 2004/0138654 A1 | 7/2004 | Goble |
| 2004/0162554 A1 | 8/2004 | Lee et al. |
| 2004/0236321 A1 | 11/2004 | Palanker et al. |
| 2004/0267254 A1 | 12/2004 | Manzo et al. |
| 2005/0021028 A1 | 1/2005 | Palanker et al. |
| 2005/0080412 A1 | 4/2005 | Ouchi |
| 2005/0177150 A1 | 8/2005 | Amoah et al. |
| 2005/0220674 A1 | 10/2005 | Shafirstein et al. |
| 2005/0234439 A1 | 10/2005 | Underwood |
| 2005/0234446 A1 | 10/2005 | Van Wyk et al. |
| 2005/0288665 A1 | 12/2005 | Woloszko |
| 2006/0069386 A1 | 3/2006 | Dubnack et al. |
| 2006/0155270 A1 | 7/2006 | Hancock et al. |
| 2006/0235450 A1 | 10/2006 | Kasahara et al. |
| 2006/0253117 A1 | 11/2006 | Hovda et al. |
| 2006/0259025 A1 | 11/2006 | Dahla |
| 2006/0259033 A1 | 11/2006 | Nesbitt |
| 2007/0100405 A1 | 5/2007 | Thompson et al. |
| 2007/0112348 A1 | 5/2007 | Eggers et al. |
| 2007/0129715 A1 | 6/2007 | Eggers et al. |
| 2007/0149966 A1 | 6/2007 | Dahla et al. |
| 2007/0179497 A1 | 8/2007 | Eggers et al. |
| 2007/0208335 A1 | 9/2007 | Woloszko et al. |
| 2007/0239156 A1 | 10/2007 | Palanker et al. |
| 2008/0004621 A1 | 1/2008 | Dahla et al. |
| 2008/0015565 A1 | 1/2008 | Davison |
| 2008/0021447 A1 | 1/2008 | Davison et al. |
| 2008/0027428 A1 | 1/2008 | Palanker et al. |
| 2008/0119842 A1 | 5/2008 | Palanker et al. |
| 2008/0125774 A1 | 5/2008 | Palanker et al. |
| 2009/0306642 A1 | 12/2009 | Vankov |
| 2012/0053583 A1 | 3/2012 | Palanker et al. |
| 2012/0143186 A1 | 6/2012 | McNall, III et al. |
| 2014/0100557 A1 | 4/2014 | Bohner et al. |

FOREIGN PATENT DOCUMENTS

| | | |
|---|---|---|
| EP | 0 672 841 A2 | 9/1995 |
| EP | 0 672 841 A3 | 9/1995 |
| EP | 0 672 841 B1 | 9/1995 |
| EP | 0 694 290 B1 | 1/1996 |
| EP | 0 697 841 B1 | 2/1996 |
| EP | 0 697 841 B2 | 2/1996 |
| EP | 0 708 618 B1 | 5/1996 |
| EP | 0 754 437 A3 | 1/1997 |
| EP | 0 754 437 B1 | 1/1997 |
| EP | 0 754 437 B2 | 1/1997 |
| EP | 0 771 176 B1 | 5/1997 |
| EP | 0 771 176 B2 | 5/1997 |
| EP | 0 820 249 B1 | 1/1998 |
| EP | 0 833 593 B1 | 4/1998 |
| EP | 0 833 593 B2 | 4/1998 |
| EP | 0 837 647 B1 | 4/1998 |
| EP | 0 858 295 B1 | 8/1998 |
| EP | 0 865 256 B1 | 9/1998 |
| EP | 0 869 742 B1 | 10/1998 |
| EP | 0 873 089 B1 | 10/1998 |
| EP | 0 882 430 A3 | 12/1998 |
| EP | 0 882 430 B1 | 12/1998 |
| EP | 0 886 493 A3 | 12/1998 |
| EP | 0 886 493 B1 | 12/1998 |
| EP | 0 887 046 B1 | 12/1998 |
| EP | 0 923 907 A1 | 6/1999 |
| EP | 0 949 886 B1 | 10/1999 |
| EP | 0 959 784 B1 | 12/1999 |
| EP | 0 959 786 B1 | 12/1999 |
| EP | 0 959 787 B1 | 12/1999 |
| EP | 0 996 378 B1 | 5/2000 |
| EP | 1 018 994 B1 | 7/2000 |
| EP | 1 025 807 A3 | 8/2000 |
| EP | 1 025 807 B1 | 8/2000 |
| EP | 1 026 996 B1 | 8/2000 |
| EP | 1 027 020 B1 | 8/2000 |
| EP | 1 034 746 A3 | 9/2000 |
| EP | 1 034 746 B1 | 9/2000 |
| EP | 1 034 747 A1 | 9/2000 |
| EP | 1 034 748 A1 | 9/2000 |
| EP | 1 036 547 A2 | 9/2000 |
| EP | 1 036 547 A3 | 9/2000 |
| EP | 1 039 862 B1 | 10/2000 |
| EP | 1 041 933 B1 | 10/2000 |
| EP | 1 050 278 A1 | 11/2000 |
| EP | 1 053 719 A1 | 11/2000 |
| EP | 1 053 720 A1 | 11/2000 |
| EP | 1 055 399 A1 | 11/2000 |
| EP | 1 061 857 B1 | 12/2000 |
| EP | 1 065 981 B1 | 1/2001 |
| EP | 1 079 746 B1 | 3/2001 |
| EP | 1 080 680 A1 | 3/2001 |
| EP | 1 080 694 A1 | 3/2001 |
| EP | 1 082 944 B1 | 3/2001 |
| EP | 1 158 917 B1 | 12/2001 |
| EP | 1 174 093 A1 | 1/2002 |
| EP | 1 179 320 A2 | 2/2002 |
| EP | 1 179 320 A3 | 2/2002 |
| EP | 1 205 155 A1 | 5/2002 |
| EP | 1 253 866 B1 | 11/2002 |
| EP | 1 257 220 B1 | 11/2002 |
| EP | 1 287 788 A1 | 3/2003 |
| EP | 1 330 201 B1 | 7/2003 |
| EP | 1 330 989 B1 | 7/2003 |
| EP | 1 344 498 B1 | 9/2003 |
| EP | 1 374 788 A1 | 1/2004 |
| EP | 1 407 719 A3 | 4/2004 |
| EP | 1 581 128 B1 | 10/2005 |
| EP | 1 599 146 B1 | 11/2005 |
| EP | 1 602 338 A2 | 12/2005 |
| EP | 1 632 191 A3 | 3/2006 |
| EP | 1 637 087 A3 | 3/2006 |
| EP | 1 693 015 A3 | 8/2006 |
| EP | 1 782 741 A2 | 5/2007 |
| EP | 1 880 686 A2 | 1/2008 |
| JP | 2001-178740 A | 7/2001 |
| WO | WO-96/39914 A1 | 12/1996 |
| WO | WO-97/23169 A1 | 7/1997 |
| WO | WO-97/27893 A1 | 8/1997 |
| WO | WO-97/48346 A1 | 12/1997 |
| WO | WO-98/03117 A1 | 1/1998 |
| WO | WO-98/03220 A1 | 1/1998 |
| WO | WO-98/19625 A2 | 5/1998 |
| WO | WO-98/19625 A3 | 5/1998 |
| WO | WO-98/43549 A1 | 10/1998 |
| WO | WO-98/56324 A1 | 12/1998 |
| WO | WO-99/03407 A1 | 1/1999 |
| WO | WO-99/03408 A1 | 1/1999 |
| WO | WO-99/03409 A1 | 1/1999 |
| WO | WO-99/09919 A1 | 3/1999 |
| WO | WO-99/16359 A1 | 4/1999 |

(56) References Cited

FOREIGN PATENT DOCUMENTS

| | | |
|---|---|---|
| WO | WO-99/20213 A1 | 4/1999 |
| WO | WO-99/30655 A1 | 6/1999 |
| WO | WO-99/32042 A1 | 7/1999 |
| WO | WO-99/40858 A1 | 8/1999 |
| WO | WO-99/49799 A1 | 10/1999 |
| WO | WO-00/09053 A1 | 2/2000 |
| WO | WO-00/41638 A1 | 7/2000 |
| WO | WO-00/54683 A1 | 9/2000 |
| WO | WO-00/62685 A1 | 10/2000 |
| WO | WO-00/62698 A1 | 10/2000 |
| WO | WO-00/62698 C1 | 10/2000 |
| WO | WO-00/71043 A1 | 11/2000 |
| WO | WO-01/35845 A1 | 5/2001 |
| WO | WO-01/60273 A1 | 8/2001 |
| WO | WO-01/95819 A1 | 12/2001 |
| WO | WO-02/11635 A1 | 2/2002 |
| WO | WO-02/19932 A1 | 3/2002 |
| WO | WO-02/102255 A1 | 12/2002 |
| WO | WO-03/005882 A2 | 1/2003 |
| WO | WO-03/005882 A3 | 1/2003 |
| WO | WO-03/024305 A2 | 3/2003 |
| WO | WO-03/024305 A3 | 3/2003 |
| WO | WO-03/024339 A1 | 3/2003 |
| WO | WO-03/028542 A2 | 4/2003 |
| WO | WO-03/028542 A3 | 4/2003 |
| WO | WO-03/061499 A1 | 7/2003 |
| WO | WO-03/068311 A2 | 8/2003 |
| WO | WO-03/068311 A3 | 8/2003 |
| WO | WO-03/090638 A1 | 11/2003 |
| WO | WO-03/092521 A1 | 11/2003 |
| WO | WO-2004/002293 A2 | 1/2004 |
| WO | WO-2004/002293 A3 | 1/2004 |
| WO | WO-2004/022155 A2 | 3/2004 |
| WO | WO-2004/022155 A3 | 3/2004 |
| WO | WO-2004/071278 A2 | 8/2004 |
| WO | WO-2004/071278 A3 | 8/2004 |
| WO | WO-2004/073752 A2 | 9/2004 |
| WO | WO-2004/073752 A3 | 9/2004 |
| WO | WO-2004/112581 A2 | 12/2004 |
| WO | WO-2004/112581 A3 | 12/2004 |
| WO | WO-2005/009213 A2 | 2/2005 |
| WO | WO-2005/009213 A3 | 2/2005 |
| WO | WO-2005/072634 A2 | 8/2005 |
| WO | WO-2005/072634 A3 | 8/2005 |
| WO | WO-2005/112806 A2 | 12/2005 |
| WO | WO-2005/112806 A3 | 12/2005 |
| WO | WO-2005/117735 A1 | 12/2005 |
| WO | WO-2005/122936 A1 | 12/2005 |
| WO | WO-2005/122938 A1 | 12/2005 |
| WO | WO-2006/002337 A2 | 1/2006 |
| WO | WO-2006/002337 A3 | 1/2006 |
| WO | WO-2006/051252 A1 | 5/2006 |
| WO | WO-2006/125007 A2 | 11/2006 |
| WO | WO-2006/125007 A3 | 11/2006 |
| WO | WO-2007/103800 A2 | 9/2007 |
| WO | WO-2007/103800 A3 | 9/2007 |
| WO | WO-2007/103800 C1 | 9/2007 |
| WO | WO-2007/143445 A2 | 12/2007 |
| WO | WO-2007/143445 A3 | 12/2007 |
| WO | WO-2010/077373 A1 | 7/2010 |

OTHER PUBLICATIONS

European Examination Report mailed on Dec. 12, 2008, for EP Application No. 04755740.0 filed on Jun. 18, 2004, four pages.

European Examination Report mailed on Sep. 2, 2010, for EP Application No. 03733930.6, filed on May 2, 2003, six pages.

Extended European Search Report mailed on May 24, 2011, for EP Application No. 07861654.7, filed on Nov. 1, 2007, eight pages.

Extended European Search Report mailed on Aug. 22, 2011, for EP Application No. 10175129.5, filed on Apr. 11, 2008, seven pages.

International Preliminary Report on Patentability mailed on May 14, 2009, for PCT Application No. PCT/US2007/023130, filed on Nov. 1, 2007, seven pages.

International Preliminary Report on Patentability mailed on Oct. 15, 2009, for PCT Application No. PCT/US2008/004460, filed on Apr. 4, 2008, six pages.

International Search Report mailed on Dec. 8, 2005, for PCT Application No. PCT/US04/19785, filed on Jun. 18, 2004, one page.

International Search Report mailed on May 15, 2008, for PCT Application No. PCT/US2007/023130, filed on Nov. 1, 2007, three pages.

International Search Report mailed on Nov. 30, 2009, for PCT Application No. PCT/US2009/030180, filed on Jan. 6, 2009, nine pages.

International Search Report mailed on Aug. 28, 2012, for PCT Application No. PCT/US2012/040799, filed on Jun. 4, 2012, five pages.

Invitation to Pay Additional Fees mailed on Sep. 24, 2009 for PCT Application No. PCT/US2009/030180, filed on Jan. 6, 2009, five pages.

Jones, H.M. et al. (Jan. 14, 1995). "Development of Pulsed Dielectric Breakdown in Liquids," *J. Phys. D: Appl. Phys.* 28(1):178-188.

Jones, H.M. et al. (Jan. 15, 1995). "Pulsed Dielectric Breakdown of Pressurized Water and Salt Solutions," *J. Appl. Phys.* 77(2):795-805.

Miller, J.M. et al. (Jun. 2003). "Precision and Safety of the Pulsed Electron Avalanche Knife in Vitreoretinal Surgery," *Arch Opthalmol* 121:871-877.

Mylrea, K.C. et al. (Jul.-Sep. 1981). "Introduction to Electrosurgery," *Journal of Clinical Engineering* 6(3):185-191.

Palanker, D. et al. (Jun. 1, 1997). "Electrical Alternative to Pulsed Fiber-Delivered Lasers in Microsurgery," *J. Appl. Phys.* 81(11):7673-7680.

Palanker, D. et al. (2002). "Effect of the Probe Geometry on Dynamics of Cavitation," *Proc. SPIE* 4617:112-117.

Supplemental European Search Report mailed on Jul. 18, 2007, for EP Application No. 04755740.0 filed on Jun. 18, 2004, four pages.

Supplemental European Search Report mailed on Jul. 3, 2008, for EP Application No. 04711134.9 filed on Sep. 14, 2005, five pages.

Written Opinion mailed on Dec. 8, 2005, for PCT Application No. PCT/US04/19785, filed on Jun. 18, 2004, three pages.

Written Opinion mailed on May 15, 2008, for PCT Application No. PCT/US2007/023130, filed on Nov. 1, 2007, five pages.

Written Opinion mailed on Nov. 30, 2009, for PCT Application No. PCT/US2009/030180, filed on Jan. 6, 2009, ten pages.

Written Opinion mailed on Aug. 28, 2012, for PCT Application No. PCT/US2012/040799, filed on Jun. 4, 2012, seven pages.

\* cited by examiner

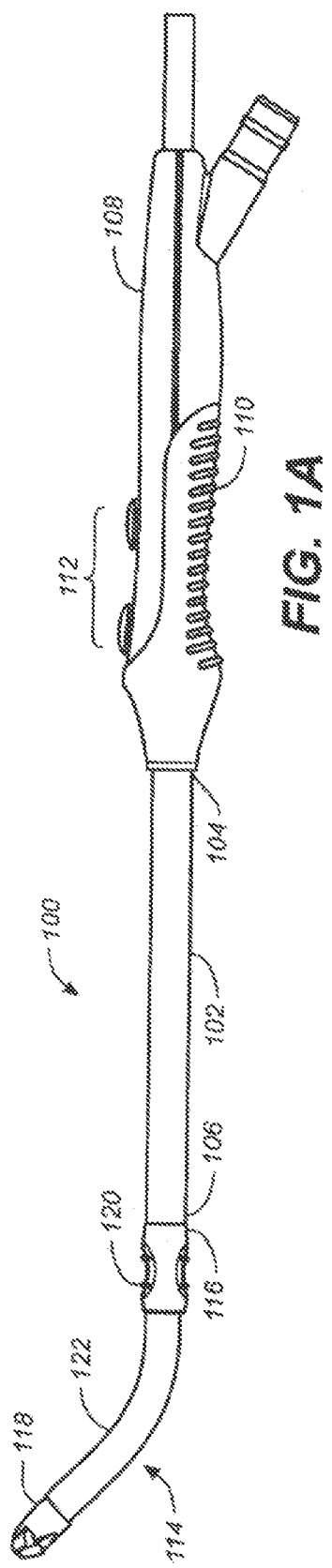
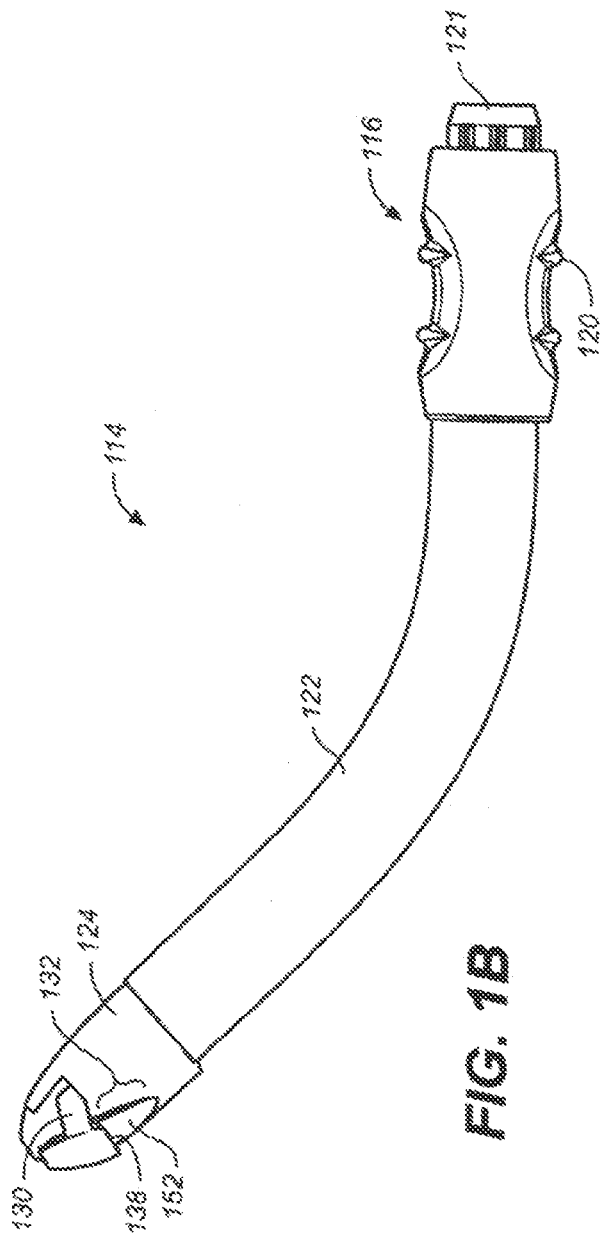
FIG. 1A
FIG. 1B

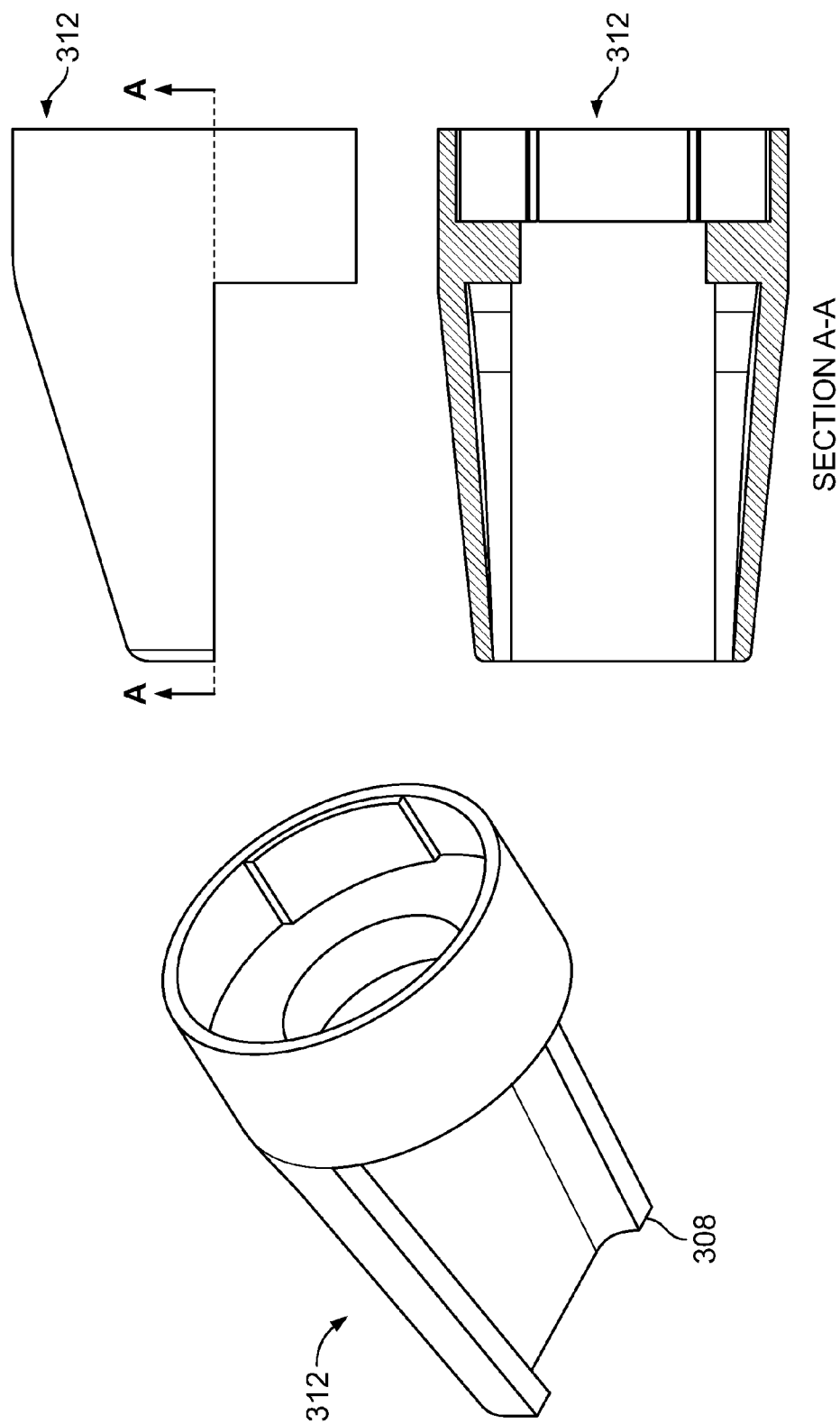

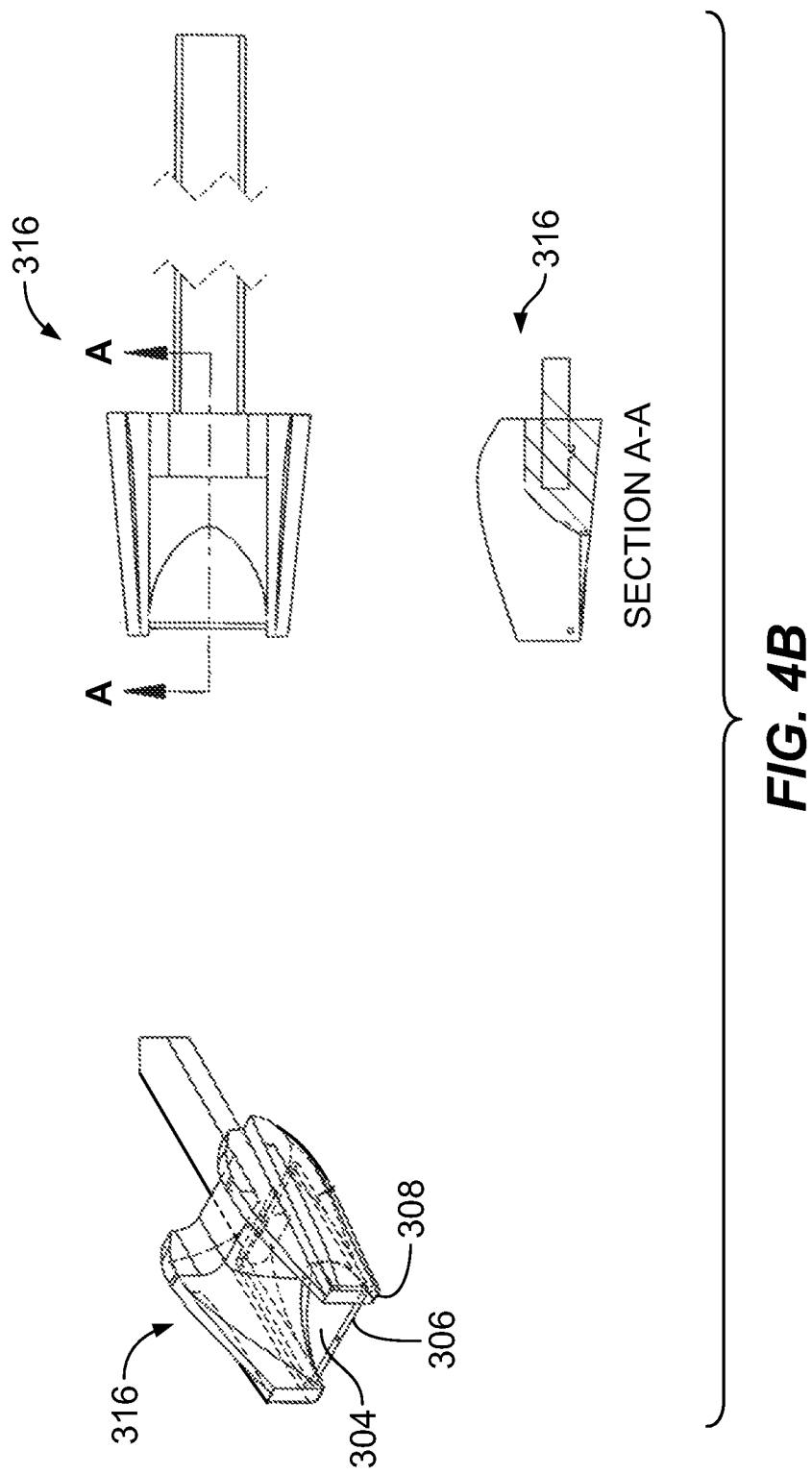

WIRE ELECTRODE DEVICES FOR TONSILLECTOMY AND ADENOIDECTOMY

CROSS-REFERENCE TO RELATED APPLICATION

This claims the benefit under 35 U.S.C. §119(e) of U.S. Provisional Application No. 61/495,853, filed Jun. 10, 2011, the contents of which is incorporated herein by reference in its entirety.

FIELD

The field is electrosurgery, and in particular, tonsillectomy and adenoidectomy.

BACKGROUND

The tonsils and adenoids are generally located in the back of the human (mammalian) nose and throat, and are part of the lymphatic system that samples bacteria and viruses entering the body. Once sampled, the immune system is activated to produce antibodies that fight infection. When bacteria and viruses become trapped in the tonsils and adenoids, these tissues are able to break down their cell wall and deliver the fragments to areas of the body that produce antibodies modeled against the fragments. However, repeated inflammation of the tonsils and adenoids impedes their ability to destroy the bacteria that become entrapped therein, resulting in bacterial colonization of these tissues. The colonies of bacteria can then serve as a reservoir for repeated infections (e.g., tonsillitis or ear infections). Tonsillectomy and/or adenoidectomy may be indicated when antibiotic treatment fails to remove the bacterial reservoir. Tonsil tissue may also need to be removed if it enlarges to the point of causing airway obstruction, which may manifest as snoring or sleep apnea. Some individuals are also born with larger tonsils that are more prone to cause obstruction. Adenoidectomy may also be required to remove adenoid tissue when ear pain persists, or when nose breathing or function of the Eustachian tubes is impaired.

The devices and techniques used for tonsillectomy and adenoidectomy will usually depend on such factors as the type and amount of tissue to be removed and surgeon preference. The two procedures are routinely performed together. A common method for tonsillectomy and adenoidectomy employs cold surgical dissection. Here tissue is removed using a scalpel or other sharp instrument such as a curette or punch device. Sharp dissection oftentimes results in heavy bleeding, which can be stemmed with electrocautery.

In addition to coagulation, electrosurgery devices (e.g., suction-tipped, blade, or needle tip Bovies) may also be employed to resect tonsil or adenoid tissue. The suction tipped Bovie typically has a hollow center to suction blood, secretions, and smoke from the surgical field, and a rim of metal for cutting and coagulation. A separate aspirator is used when blade and needle tip Bovies are used. Although the use of Bovies reduces blood loss intraoperatively in comparison to cold techniques, it is associated with increased postoperative pain due to spread of the thermal injury from the heat of electrosurgery (average temperatures are above 300° C.). Despite their increased thermal injury profile, use of the Bovie remains the most popular method of tonsil removal in the U.S. due to its speed, convenience, universal availability, and surgeon familiarity with the device.

Other energy-type devices have been commercialized that attempt to minimize thermal injury. These include the Harmonic Scalpel® system (Ethicon Endo-Surgery, Cincinnati, Ohio) (ultrasonic energy), lasers (e.g., KTP, Nd:YAG, or $CO_2$ lasers), and Coblation® devices (Arthrocare, Austin, Tex.) (bipolar radiofrequency ablation). However, the decrease in thermal injury provided by these devices is questionable. Even if they do result in less thermal injury, it is offset by reduced control of bleeding and surrounding tissue trauma, longer operative times, or less precise cutting. Some of the instruments also obscure the surgical field and are difficult to maneuver due to their large size.

When Coblation® devices are employed, the procedure requires saline delivery in order to establish an electrosurgical effect. Pre-operative time is prolonged due to the inclusion of the saline delivery set-up. Coblation® device aspiration lumens also periodically clog during the procedure, which causes saline to pool in the patient's throat. The pooled saline must then be suctioned using a separate aspirator. Additionally, the Coblation® device lumen typically has to be manually cleared in order to finish the surgery.

Accordingly, new devices for resecting tonsil and adenoid tissue would be useful. In particular, devices that precisely cut tonsil and adenoid tissue while effectively controlling bleeding and surrounding tissue trauma would be desirable. Devices that provide easier access to the tonsils and adenoids and manipulation of those tissues would also be desirable.

SUMMARY

Described here (but not limiting) are electrically "monopolar" electrosurgical devices that optimize many functions required in performing tonsillectomy or adenoidectomy while minimizing side-effects (the return electrode is applied to the patient remote from the active electrode). For example, the precise cutting of tissue is provided by a thin layer of plasma that surrounds the electrode edge. In some instances the plasma is formed with pulsed radiofrequency (RF) energizing waveforms having a lower range of duty cycles so that tissue has time to cool between pulses. This coupled with the mostly insulated tips helps to reduce thermal damage by limiting the extent of thermal diffusion from the electrode into surrounding tissue. Continuous or 100% duty cycle energizing waveforms may also be employed when faster cutting is desired. When hemostasis is needed, suction and plasma may be directly applied to the target area to mechanically and electrically stop the bleeding. Tension of the electrode surface(s) against the tissue is generally optimized with a configuration where suction is applied through the electrode or in very close proximity thereto. The aspiration port being closely associated with the blade allows a "dry field" surgical technique. This is advantageous here because it allows a concave blade to function well unlike the case with a wet field. This is because current flows from the blade to the tissue only via the part of the blade in actual tissue contact with the dry field. Further, the suction decreases the width of the tissue in contact with the blade, further reducing the contact area and also further drying the tissue. Given that it may be difficult to access the portions of the oropharynx and nasopharynx where the tonsils and adenoids are located, the devices described herein may be designed with one or more malleable portions so that they can be shaped to improve access to these regions and/or accommodate variations in patient anatomy.

It has been found that for ENT (ear-nose-throat) surgery as described here, a monopolar approach is advantageous because the remote return electrode guarantees good electrical contact. In contrast, given the nature of such energizing, a bipolar device with both electrodes on one shaft makes good electrical contact for the return electrode difficult.

The electrosurgical devices generally include an elongate body having a proximal end, a distal end, and an aspiration lumen extending therethrough, an interchangeable tip removably attached to the distal end of the elongate body, and a handle at the proximal end of the elongate body where control mechanisms for cutting and coagulation are located. The interchangeable tip typically also has a proximal end, a distal end, and a tip lumen that is fluidly connected to the aspiration lumen of the elongate body. A housing that is secured to the distal end of the interchangeable tip will usually have an aperture and an integrated blade assembly, e.g., an electrode assembly, that includes an active electrode. The phrases "blade assembly" and electrode assembly" are used herein interchangeably. In some variations, the active electrode is a wire or loop electrode. The blade assembly or portion thereof may define an aspiration port that communicates with the aperture of the housing.

The devices generally include a connector at the proximal end of the interchangeable tips for removably attaching them to the elongate body. In some variations, the connector comprises a compressible barrel and one or more tabs that are located circumferentially around the connector. The compressible barrel may be inserted into the distal end of the elongate body to create a friction fit between the components and to thereby removably attach them to one another. The one or more tabs may be used to attach an ergonomic finger grip to the connector that may make insertion and removal of the interchangeable tip easier.

The interchangeable tips may be specifically configured for adenoidectomy or tonsillectomy. For example, when adenoidectomy is to be performed, the devices may include a blade assembly that optimizes tissue removal using a raking motion. Here the blade assembly may include an active electrode that has a cutting edge and a flat coagulation surface. A plurality of arms extending from the active electrode may secure the active electrode to the housing. The arms may have an angle that positions the cutting edge against the tissue in a manner that allows it to be easily and precisely scooped or shaved into the aspiration port. The particular arm angle may also be useful in achieving hemostasis by optimizing the position of the coagulation surface against the tissue. Alternatively, the electrode is a wire electrode.

When tonsillectomy is to be performed, the devices may include a blade assembly having a curved and tapered active electrode. This curvature may result in a more precise tonsil resection because the electrode surface approximately conforms to the contour of tonsil tissue. The curved and tapered electrode may also define an aspiration port therethrough. Here bleeding may be more effectively controlled since suction may be applied directly through the aspiration port of the electrode when the device is in the coagulation mode. This would combine mechanical pressure with plasma coagulation to achieve hemostasis.

The interchangeable tips may also be configured to be malleable so that their shape can be tailored to navigate access to the tissues or accommodate variations in patient anatomy. In some instances the interchangeable tips may be made for single use. Kits including one or more interchangeable tips are also contemplated.

Methods for resecting tonsil or adenoid tissue may generally include applying a pulsed electrical signal to the active electrode of the devices described herein to form a plasma on the active electrode, and cutting or coagulating the tissue with the plasma. In some variations, suction is applied simultaneously with proximal movement of the electrode to suction cut the tissue. In other variations, the tissue is coagulated while suction is simultaneously applied. In yet further variations, the methods will include exchanging one interchangeable tip, e.g., a tonsillectomy tip, with another interchangeable tip, e.g., an adenoidectomy tip.

BRIEF DESCRIPTION OF THE DRAWINGS

FIG. 1A depicts a side view of an exemplary electrosurgical device with an adenoidectomy tip.

FIG. 1B depicts an expanded side view of the adenoid tip shown in FIG. 1A.

FIGS. 4A and 4B depict in various views the two main components of the housing shown in FIG. 3.

DETAILED DESCRIPTION

Figure 1C:
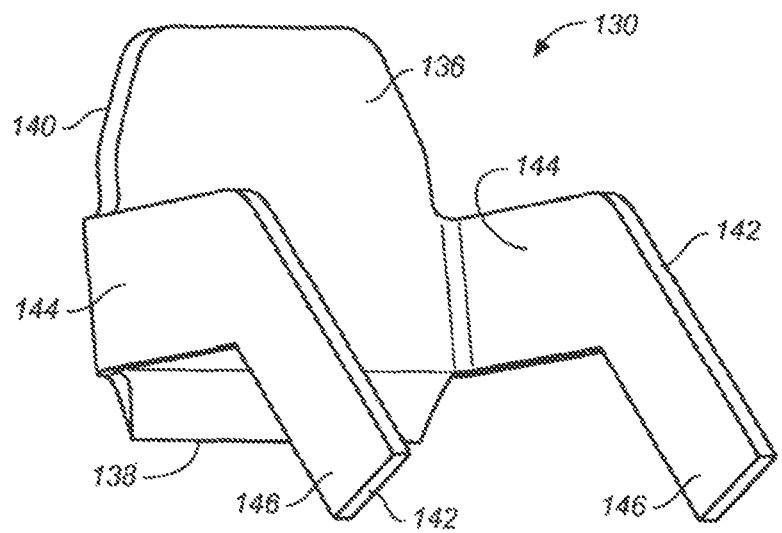
FIG. 1C is an expanded perspective view of the blade assembly shown in FIGS. 1A and 1B.

Described here are electrosurgical devices that can be customized for either adenoidectomy or tonsillectomy. Customization may be provided by the use of interchangeable tips that can be removably attached to the elongate body of the device. Specifically, the design of the blade assemblies and location of the aspiration port from which suction is applied may be varied to optimize manipulation, cutting, and hemostasis of the tissue being operated on.

The present electrosurgical devices are generally monopolar instead of bipolar. Both types of devices use high frequency alternating current and a pair of electrodes, one designated the active electrode and the other the return electrode. However, the difference lies in the placement of these electrodes. In a monopolar device, current is passed from the active electrode through the patient's body to a grounding pad (return electrode) placed on the body, usually the thigh or shoulder. A monopolar device may be particularly useful in tonsil and adenoid surgery because contact with the body is guaranteed. In a bipolar device, the active and return electrodes are both placed at the site of electrosurgery, for example, on the same shaft of the device, and electrosurgery occurs only on the tissue on the active electrode(s) if there is a conductive path back to the return electrode.

The devices will generally include an elongate body having a proximal end, a distal end, and an aspiration lumen extending therethrough. Depending on the materials used, all or a portion of the elongate body may be formed to be stiff, flexible, or malleable. Exemplary materials for making the elongate body include, without limitation, fluoropolymers; thermoplastics such as polyetheretherketone, polyethylene, polyethylene terephthalate, polyurethane, nylon, and the like; and silicone. Another material is fluoroelastomer.

The elongate body may be between about 5.0 cm to about 20 cm in length. For example, the elongate body may be between about 5.0 cm to about 15 cm, between about 5.0 cm to about 10 cm, or between about 5.0 cm to about 8.0 cm in length. In some instances, the elongate body may be about 8.0 cm in length. In other instances the devices lack an elongate body, and the interchangeable tip is directly connected to the handle.

In some variations, the elongate body is coated with a lubricious polymer to reduce friction between the mucosa and device during the procedure. Lubricious polymers are well known in the art, and are typically hydrophilic. Exemplary hydrophilic polymers that may be used as lubricious coatings include, without limitation, polyvinyl alcohol, polyethylene glycol, polyvinyl pyrrolidone, cellulosic polymers and polyethylene oxide.

A handle is usually coupled to the proximal end of the elongate body that allows the surgeon to hold the device. The handle may include a hand grip on the bottom and a pad with at least two control buttons on the top. The control buttons may be depressed to activate electric switches for turning on the cutting or coagulation regimes. The button pad and hand grip are incorporated into the handle using spring clips or other well-know attachments and conventional techniques such as overmolding. A standard electrical connector and cable may be used with the handle to connect electrical leads to a generator. The handle may be between about 5.0 cm to about 30 cm, about 5.0 cm to about 25 cm, about 5.0 to about 20 cm, or about 5.0 cm to about 15 cm in length. In one variation, the handle is about 20 cm in length.

The aspiration lumen of the elongate body continues through the handle to a suction connector, which in turn connects tubing to a collection canister. The dimensions of the handle may be varied such that it is comfortably held in a hand, yet able to be manipulated during tonsillectomy and adenoidectomy. In some variations, the handle may be made for single use. As used herein, the term "suction handle" shall refer to the handle when coupled to the elongate body.

An interchangeable tip, as further described below, may be removably attached to the distal end of the elongate body. The interchangeable tip will typically have a proximal end, a distal end, and a tip lumen that is fluidly connected to the aspiration lumen to allow continuous flow of fluids, tissue, smoke, etc. away from the surgical field. The length of the interchangeable tip varies, but may be from about 1.0 cm to about 15 cm. For example, the adenoidectomy tip may be between about 5.0 cm to about 10 cm, and the tonsillectomy tip may be from about 1.5 cm to about 5.0 cm. In one variation, the adenoidectomy tip is about 9.0 cm. In another variation, the tonsillectomy tip is about 2.5 cm. The materials used to make the elongate body may also be employed in forming the interchangeable tip.

In one variation, the interchangeable tip is malleable. Malleability may be provided by wires running through the wall of the elongate body that are capable of being shaped by bending the elongate body. For example, the wires may be made from stainless steel or alloys thereof, nickel-titanium alloy, etc. Malleability may also be provided by forming the elongate body or portions thereof with metals or polymers that can be shaped. In some variations, joints or hinges are included. By having the ability to manipulate the shape of the interchangeable tip, it may be easier and quicker to access the tonsils and adenoids with the devices and easier to accommodate anatomical variations in that area. The interchangeable tips may be bent directly, e.g., by finger manipulation, or remotely through cables or wires using mechanisms commonly employed with steerable catheters. The interchangeable tips may be designed for single use.

The devices generally include a connector at the proximal end of the interchangeable tips for removably attaching them to the elongate body. An ergonomic finger grip may be used on the connector that may ease insertion and removal of the interchangeable tip. In some variations, the interchangeable tip may be configured to rotate about the connector. The connectors may be configured to removably attach to the elongate body by friction fit mechanisms. For example, they may include a compressible component that has a larger diameter when not connected to the elongate body. Compression of the component typically allows it to be slidingly engaged with the elongate body at which point the component is capable of expanding to its uncompressed diameter against the internal wall of the elongate body. In one variation, the connector comprises a compressible barrel and one or more tabs that are located circumferentially around the connector. The compressible barrel may be inserted into the distal end of the elongate body to create a friction fit between the components and to thereby removably attach them to one another. The one or more tabs may be used to attach an ergonomic finger grip to the connector that may make insertion and removal of the interchangeable tip easier.

Connection between the elongate body and interchangeable tip may also be supplied by locking-unlocking mechanisms. For example, the interchangeable tip may include a groove or channel, e.g., a L-shaped channel, in its wall configured so that upon receipt of a pin or other protrusion on the elongate body, the interchangeable tip may be rotated to be locked in placed. Other tongue-and-groove type locks and mechanisms including depressible pins or tabs are also contemplated.

The electrosurgical devices described here also generally include a housing at the distal end of the interchangeable tip for holding and securing the blade assembly thereto. The housing may be a single unit component or be made from multiple components. For example, the housing may be made by pressing together two components, an upper portion and lower portion. In some variations, the housing is configured with a blunt nose. In other variations, the housing is designed with a taper.

The housing may include an aperture through which suction can be applied to the tissues. The aperture may be of any shape and size so long as it provides an opening for aspiration of smoke, tissue, fluids, etc. For example, the aperture may be spherical, elliptical, egg-shaped, rectangular, triangular, diamond-shaped, or heart-shaped. These shapes are not meant to be limiting. When tissue is to be aspirated, the aperture may be larger than conventional suction openings. For example, the aperture may have a diameter from about 0.1 cm to about 1.0 cm. In some variations, the aperture diameter is larger than about 0.4 cm or about 0.5 cm.

In addition, the housing may be made from transparent materials or include a marker to aid visualization or provide an electrode locator in the surgical field. Materials with suitable transparency are typically polymers such as acrylic copolymers, acrylonitrile butadiene styrene (ABS), polycarbonate, polystyrene, polyvinyl chloride (PVC), polyethylene terephthalate glycol (PETG), and styrene acrylonitrile (SAN). Acrylic copolymers that may be particular useful include, but are not limited to, polymethyl methacrylate (PMMA) copolymer and styrene methyl methacrylate (SMMA) copolymer (e.g., Zylar 631® acrylic copolymer).

A blade assembly may be integrated within the housing, and generally includes the active electrode. The active electrode typically defines a cutting edge. The edge, however, is not like that of an ordinary knife which does the cutting solely via mechanical application to the tissue being cut. Instead here the edge of the electrode focuses the electric field induced by the applied electrical signal. This field that is concentrated at the edge generates a local plasma discharge. In some instances, the edge is formed by the onlay of metal foil. The tissue cutting may be assisted by mechanical force supplied by the edge of the electrode, as in conventional cutting, or by application of suction.

The active electrode may be made from any material having suitable electrical properties. For example, the active electrode may include without limitation, metals such as molybdenum, nickel, platinum, stainless steel, tantalum, titanium, tungsten, and alloys thereof. Thickness of the active electrode may be from about 0.1 mm to about 1.0 mm thick with an edge of about 10 μm to about 70 μm in thickness. In one variation, the active electrode thickness is about 0.25 mm (0.01 inch). In another variation, the thickness is about 0.025 mm (0.001 inch). The active electrodes may be etched or stamped or machined out of a large sheet of metal, which has been annealed for hardness. The electrodes may be made from layers, or multiple metals, alloys, or in part from non-conductive materials.

An electric insulating layer may be overlaid upon the active electrode to mostly cover it but leaving an exposed edge or surface that would be used for cutting or coagulation. The insulation is typically a coating of glass or ceramic approximately 0.005 mm to 0.5 mm thick, or in some instances approximately 0.01 mm to 0.2 mm thick. When glass insulation is used, it may be applied by a conventional process of dipping each relevant component prior to assembly in liquid (molten) glass and then annealing the glass. The glass insulation may also be applied by spraying.

The configuration of the blade assembly may vary depending on the intended use of the electrode. For example, technical features that enhance removal of adenoid tissue may differ from other features of interest in tonsillectomy. These design features are further elucidated below.

Adenoidectomy Tip

Adenoid tissue, which lies at the back of the nose/throat, may be removed through the mouth or nose, but typically through the mouth under general anesthesia. Thus, not only are the adenoids difficult to get to, but the presence of an endotracheal tube further cramps an already limited surgical field. The adenoid tips described here are interchangeable tips specifically configured to address many of these difficulties with adenoidectomy.

In one variation, as illustrated in FIG. 1A, electrosurgical device 100 includes an elongate body 102 having a proximal end 104 and a distal end 106. Proximal end 104 is coupled to a handle 108 where a finger grip 110 and pair of control buttons 112 are located. Adenoid tip 114 also has a proximal end 116 and a distal end 118, and is removably attached to the elongate body distal end 106 by a connector 120 positioned at the elongate body distal end 106. Here connector 120 includes a compressible basket 121 that can be depressed and slid into the distal end of the elongate body where it will then decompress to expand and create a friction fit against the internal wall of the elongate body (FIG. 1B). The elongate body 102 may be permanently or removably attached to the handle 108, but will typically be permanently attached. Adenoid tip 114 is malleable and can be bent, as shown in FIG. 1A. Here the adenoid tube 122 comprises a flexible material such as polyurethane, and includes two lumens (not shown) within its wall where bendable wires (not shown) run longitudinally between the adenoid tip distal end 118 and proximal end 116. Additional lumens and wires may be employed as desired.

Although shown as bent upwards, the adenoid tip may be bent in other directions, so long as the device materials or functionality is not compromised. For example, the adenoid tip may be bent to form an angle with the elongate body of up to about 45°, up to about 60°, or up to about 90° or more with respect to the horizontal axis of the elongate body. Adenoid tip 114 may also be rotated to any angle about the axis of the connector 120. As previously mentioned, the bendable nature of the adenoid tip allows easier access to the adenoids. It also provides more precise positioning of the active electrode.

The adenoid distal tip also includes a housing for holding the blade assembly. As shown in FIGS. 1B and 1D, housing 124 is comprised of an upper portion 126 and a lower portion 128 that integrate a blade assembly 130 when both portions are joined together. Upper 126 and lower 128 portions may be joined by snap fitting, adhesives, welding, etc. The lower portion 128 may have an aperture 132 that defines an aspiration port 152 when the blade assembly 130 is integrated into the housing 124. In some variations, the housing may be formed using a single component instead of a plurality of components.

Figure 1D:
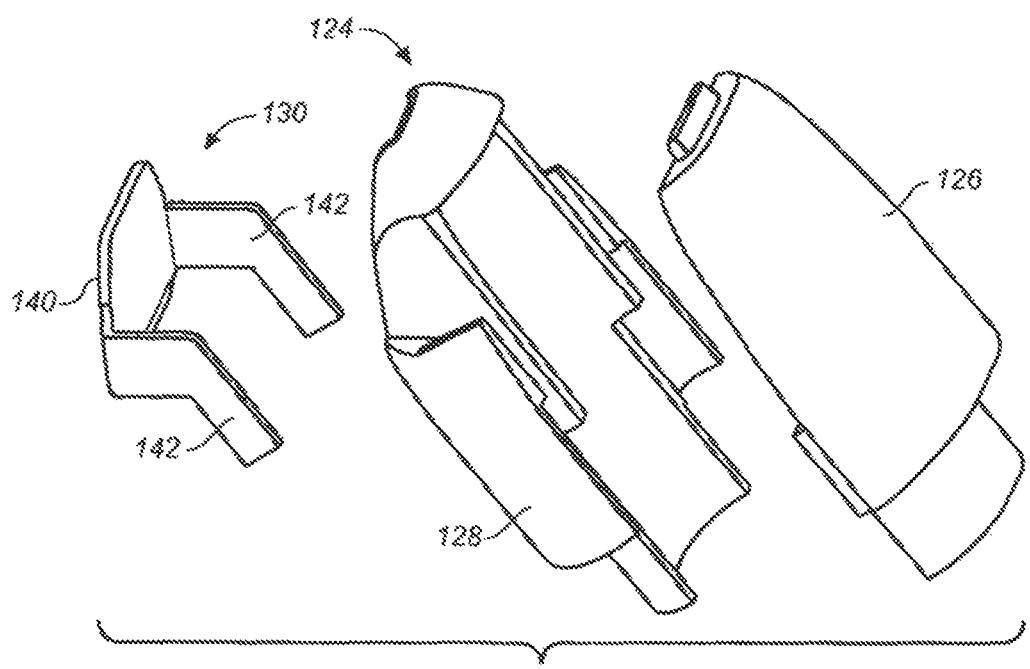
FIG. 1D shows the components of the housing in FIGS. 1A and 1B and how they are joined to integrate the blade assembly of FIG. 1C.
Figure 1E:
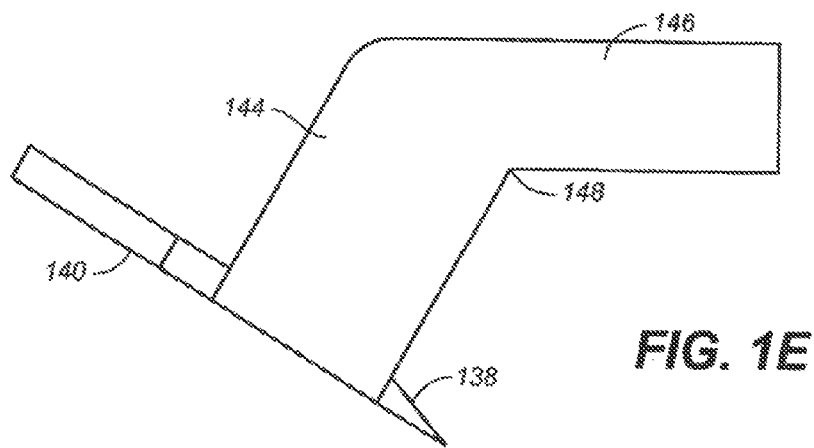
FIG. 1E is an expanded side view of the blade assembly shown in FIGS. 1A-1D.
Figure 1F:
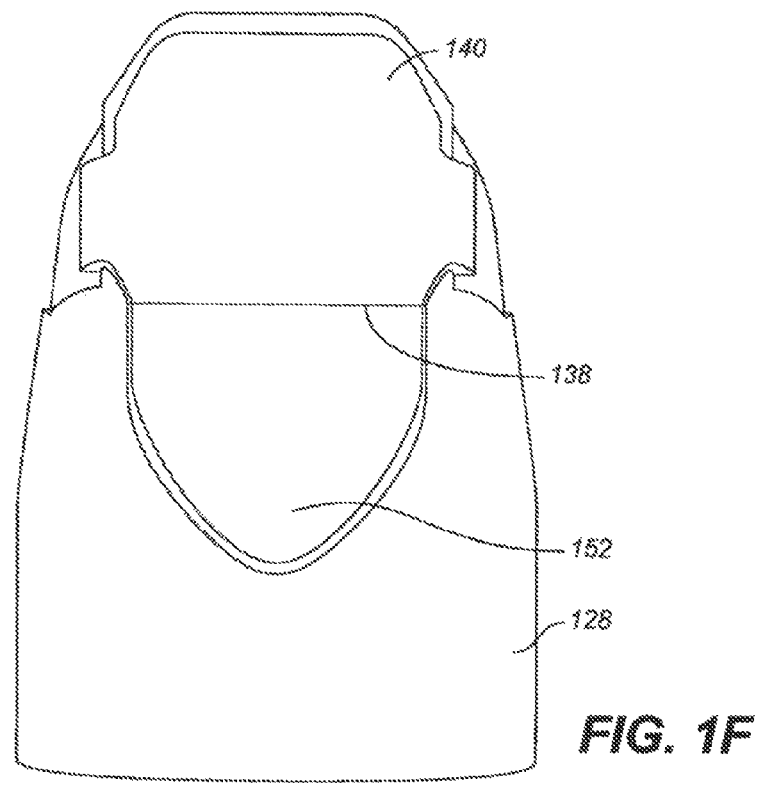
FIG. 1F shows an expanded inferior view of an exemplary housing and blade assembly for adenoidectomy.

As shown in the enlarged housing-blade assembly of FIG. 1F, the housing 124 and integrated blade assembly 130 may define an aspiration port 152, as explained above, through which suction is applied to aspirate fluids and smoke. However, the aspiration port 152 will generally also be dimensioned so that the device is capable of aspirating tissue through the port. In such instances, the port in cross-section may be spherical, ellipsoid, egg-shaped, rectangular, triangular, diamond-shaped, or heart-shaped, and thus wider than conventional suction openings. Here the aspiration port is about 0.1 cm to about 1.5 cm along its major axis and about 0.1 cm to about 1.0 cm along its minor axis. It is understood that these dimensions are exemplary and not limiting.

Bringing the upper and lower housing portions together with the blade assembly therebetween integrates the blade assembly into the housing. Here the housing is made from a transparent polymer such as Zylar 631® acrylic copolymer (SMMA copolymer) so as not to block visualization at the adenoid tip distal end 118. Although not shown here, a marker can also be included on the surface of upper housing portion 126 to indicate the blade location underneath.

Turning to FIG. 1C, blade assembly 130 includes an active electrode 136 having a cutting edge 138 and a coagulation surface 140. A plurality of arms 142 having a first portion 144 and a second portion 146 secure the active electrode 134 to the housing 124. The arms may be secured to the housing with medical grade adhesives such as cyanoacrylate or epoxy adhesives, and other adhesives, which are well known. Referring to FIG. 1E, first 144 and second 146 arm portions form an angle 148 of about 110° to about 140°. In one variation, a 120° angle is defined between the first 144 and second 146 portions. This angle may optimize opposition of the coagulation surface 140 onto tissue to effectively achieve hemostasis. Further, the angle 148 may optimize the point of contact of plasma to the tissue from the cutting edge 138 to effect a more precise cut as well as resection of tissue while minimizing clogging of the aspiration port.

Figure 1G:
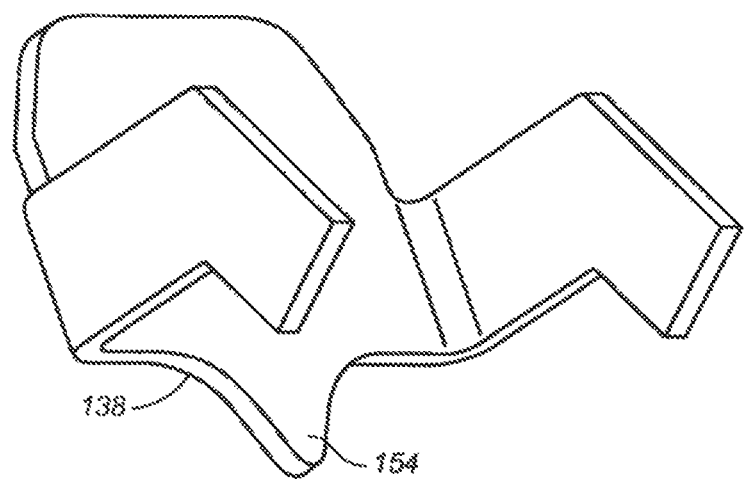
FIG. 1G depicts a variation of the cutting edge that may be used in the blade assembly for adenoidectomy.

In another variation, as shown in FIG. 1G, the cutting edge 138 may be shaped to include a leading edge 154. The leading edge may aid initiation of plasma cutting and more effectively remove adenoid tissue. In some variations, the leading edge may extend about 0.2 mm to about 2.0 mm from the cutting edge.

After the blade assembly is integrated into the housing, cutting edge 138 defines an aspiration port 152 with the aperture 132. With this adenoid tip configuration, cut adenoid tissue is directly and immediately suctioned into the aspiration port. Thus, proximal movement (movement toward the operator) of the adenoid tip while simultaneously maintaining suction may result in shaving strips of tissue.

Some variations of the adenoid tip include a wire as the active electrode. Compared to the other electrode configurations described herein, use of a wire electrode may particularly improve the cutting performance of the adenoid tip. This is because the decreased surface area of the wire generally produces less eschar build up, and thus, less sticking of tissue to the electrode. Furthermore, given that cutting is quicker with a wire electrode, contact of the wire electrode with adenoid tissue is less, resulting in decreased thermal injury to the adenoid tissue in comparison to the electrode configuration depicted in FIGS. 1A-1G (see Example 2). Another advantage of the wire design, e.g., instead of using the active electrode shown in FIGS. 1A-1G, is that it allows greater freedom of movement during the adenoidectomy procedure. For example, with the active electrode depicted in FIGS. 1A-1G, adenoid tissue would have to be approached at a specific angle because cutting of the tissue can only be made effectively when made perpendicular to the adenoids. Given the limited operative field, exposure of the adenoids is already difficult. Limiting the angle of approach would thus further frustrate the procedure. When a wire electrode is employed in the electrode assembly, cutting is not orientation specific. Another benefit is that a wire electrode is generally easier to manufacture than the active electrode of FIGS. 1A-1G.

The wire may be completely embedded within the material of the housing except for the portion that extends across the housing aperture at the distal end of the adenoid tip. The wire may be embedded by overmolding the wire into a slot provided in the housing. Seating the wire in the slot may also recess the wire a certain distance from the distal end of the adenoid tip. For example, the wire may be recessed from the distal end of the adenoid tip a distance ranging from about 0.0005 inch (0.013 mm) to about 0.20 inch (5.1 mm). The wire may be of any suitable geometry, but will typically be round or circular in cross-section, and have a diameter ranging from about 0.008 inch (0.20 mm) to about 0.010 inch (0.25 mm). In another variation, the diameter ranges from about 0.005 inch (0.0125 mm) to about 0.020 inch (0.5 mm). In one variation, the wire has a diameter of about 0.008 inch (0.20 mm).

Figure 3:
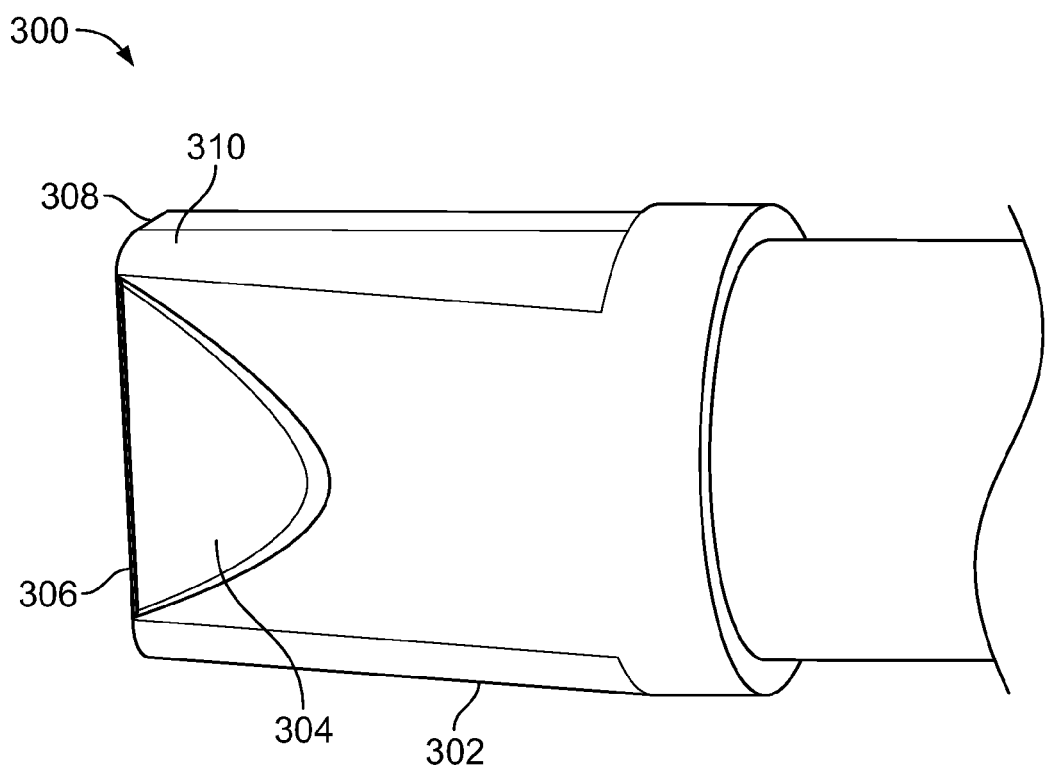
FIG. 3 is an inferior view (showing the bottom surface) of an exemplary adenoid tip including a wire as the active electrode.

As previously stated, the housing may be of any suitable dimension and geometry. However, when a wire electrode is used, the housing configuration shown in FIGS. 3 and 4A-4B may be particularly suitable. Referring to FIG. 3, adenoid tip 300 includes a housing 302 having a triangular shaped aperture 304. A wire electrode 306 extends across the aperture 304 at the distal end 308 of the adenoid tip 300. The wire electrode 306 is fully encapsulated, i.e., there is no exposed metal, within the material of the housing except for the portion that extends across the aperture 304. Wire electrode 306 is seated in a slot 310 so that the exposed portion of the wire electrode 306 is recessed from the distal end 308 of the adenoid tip 300.

Housing 302 is comprised of an upper portion and lower portion, as better shown in respectively FIGS. 4A and 4B. In FIG. 4A, upper portion 312 (shown in perspective in the upper left part of the figure) has a length of about 0.440 inch (11.18 mm) and is configured to be tapered toward its distal end 308. The taper (shown in the side view, upper right of the figure) extends over a distance of about 0.315 inch (8.0 mm). As shown in the cross-section (lower right in the figure) taken along line A-A, the width of an opening at the distal end 308 is about 0.200 inch (5.1 mm). FIG. 4B shows the lower portion 316 of housing 302 (in an x-ray view, left part of the figure). Here the wire 306 is embedded within the material of the housing lower portion 316 except for the part that extends across triangular shaped aperture 304. The wire 306 is also shown recessed a small distance from the distal end 308. The length of housing lower portion 316 may be about 0.315 inch (8.0 mm). The aperture 304 may be about 0.144 inch (3.7 mm) in length and about 0.170 inch (4.3 mm) in width (at its widest part) (shown in side view, upper right of the figure). The wire 306 will usually extend across the aperture 304 at or near its widest part. Accordingly, in FIG. 4B, the exposed portion of the wire is about 0.170 inch (4.3 mm) long. The housing 302 will generally be configured with a profile suitable for accessing and operating on the adenoids. Is some variations, and as shown in the cross-section (lower right of the figure) taken along line A-A in FIG. 4B, the lower portion of the housing 316 has a smooth, gradually tapering profile.

The upper portion 312 and lower portion 316 are brought together to make the housing 302. The upper and lower portions may be joined by methods previously described. It is understood that features such as tabs, pins, barbs, hooks, etc., and their corresponding grooves, channels, depressions, and the like, may be included to mate the upper and lower portions. The upper and lower portions may be fixedly or removable secured together.

Tonsillectomy Tip

The tonsils are located on either side of the throat and removed under general anesthesia. In this procedure, the unattached end of the tonsil is usually grasped with forceps while an incision is made at the other end to remove it from the throat. Thus, similar to adenoidectomy, access is also difficult and the surgical field cramped. The tonsillectomy tips described here are interchangeable tips specifically configured to address many of these difficulties with tonsillectomy.

The suction handle (handle with the elongate body attached) and connector are generally of the same configuration and made from the same materials as described for the adenoidectomy tips. The tonsillectomy tips may also be malleable and provide the same advantages as those previously described. Further, the housing, blade assembly, and active electrode are typically made with the same materials. However, their configuration will differ.

Figure 2A:
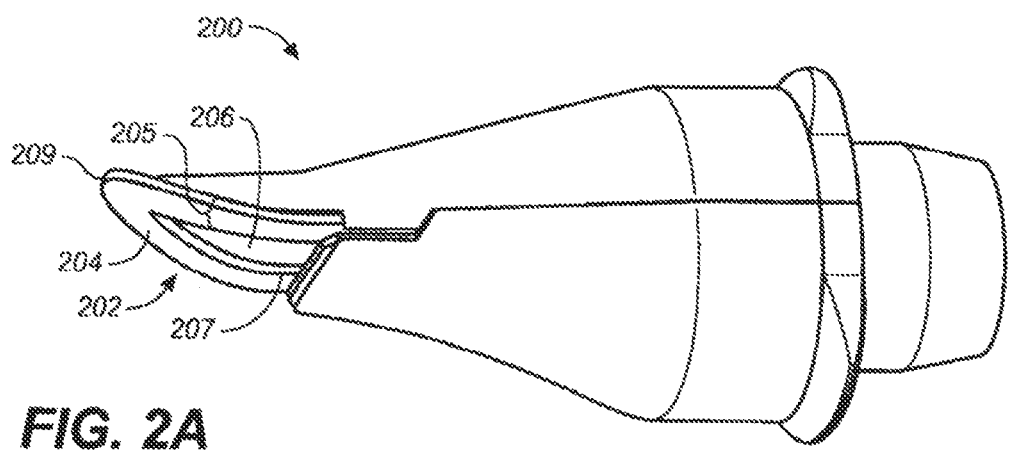
FIG. 2A depicts an exemplary housing and blade assembly for tonsillectomy.

In one variation, as depicted in FIG. 2A, the tonsillectomy tip has a housing 200 that is tapered. Blade assembly 202 is integrated within the housing 200. An opening in the active electrode 204 defines an aspiration port 206 through which suction may be applied to a tissue surface, usually the tonsil bed, as explained above. A rim of active electrode results that has a rim thickness 205 from about 0.5 mm to about 3.0 mm. The rim is insulated except for a about a 5 mm to about a 20 mm portion running along the outer edge 209. About a 2 mm to about a 15 mm exposed (uninsulated) portion may also run along the inner edge 207. Upon application of an energizing electrical signal (waveform), pulsed or continuous, plasma may be formed along the inner 207 and/or outer 209 edges of the rim to cut or coagulate tissue. As previously mentioned, cutting precision is typically not a result of the degree of sharpness of the electrode edge, and is not the case here. However, in some variations, one or more sides of the active electrode may be sharpened to form about a 10° to 40° edge.

Figure 2B:
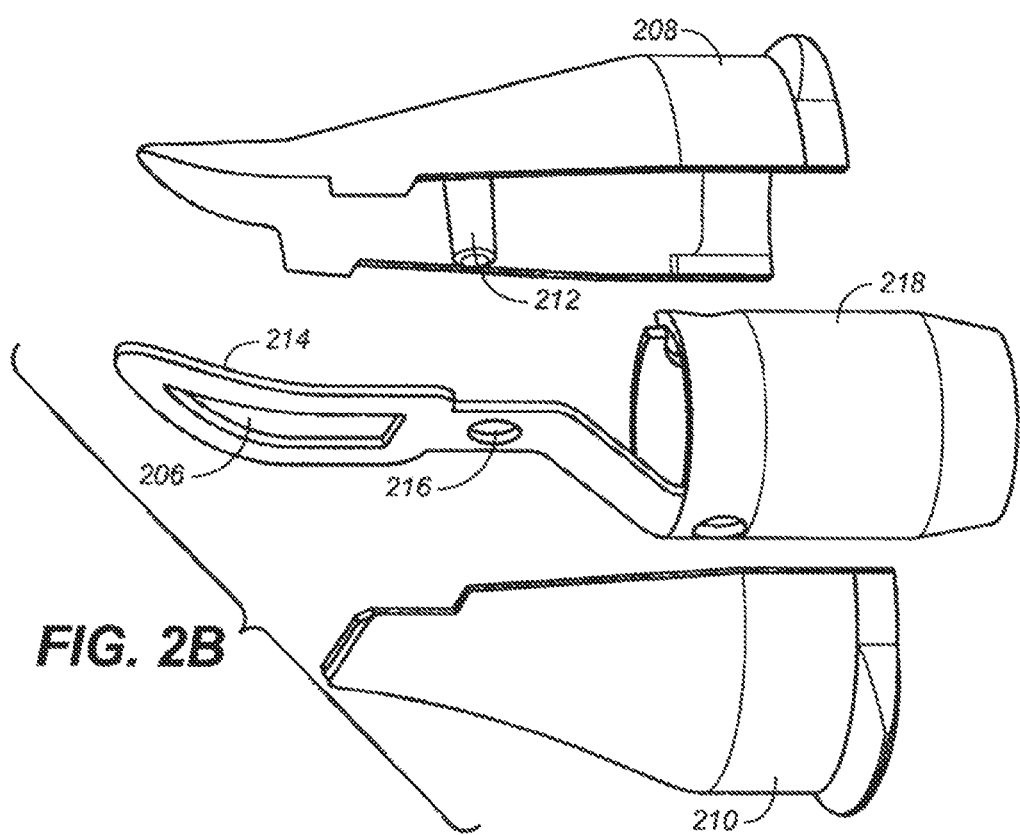
FIG. 2B shows the components of the housing in FIG. 2A and how they are joined to integrate the blade assembly also shown in FIG. 2A.

Although shown as a triangular shaped opening in FIGS. 2A and 2B, the aspiration port 206 may take various other shapes. The triangular configuration of the aspiration port may optimize suction at the tip of the device without compromising the preciseness of tissue dissection.

The active electrode may have a length from about 0.1 cm to about 1.5 cm. In one variation, the active electrode has a length of about 0.4 cm. At its widest portion, the active electrode has a width from about 0.1 cm to about 1.0 cm. In some instances, the active electrode has a width of 0.4 cm. The active electrode may also be configured with an upward curve so that it approximately conforms to the curvature of the tonsil (e.g., the palatine tonsil). This upward angle of the active electrode may be of any degree. For example, the upward angle may be from about 5° to about 60°. In some variations, the upward angle is about 30°.

The relationship between the housing and blade assembly components of FIG. 2A is further detailed in FIG. 2B. In FIG. 2B, housing 200 is shown as being formed by an upper portion 208 and a lower portion 210. A pin 212 extending inferiorly from the internal surface of the upper portion 208 is threaded through a hole 216 of the blade assembly 214 to integrate the blade assembly 214 within the housing 200. An adhesive may further be used to secure the housing and blade assembly components to one another.

The housing in FIGS. 2A-2B is shown as tapered, but need not be. In this variation, upper portion 208 is longer than bottom portion 210. The upper portion 208 will generally be from about 0.3 cm to about 3.0 in length. The bottom portion 210 will generally also be from about 0.3 cm to about 3.0 cm in length. The difference in length between the upper and lower portions results in complete coverage of the aspiration port 206 on the top of the active electrode 204 but only partial coverage of the aspiration port 206 on the bottom of the active electrode 204. With this configuration, suction may be provided through the undersurface of the active electrode. The aspiration port 206 may be from about 0.03 cm to about 0.5 cm wide, and about 0.03 cm to about 1.0 cm in length. In one variation, the aspiration port is about 0.17 cm in width and about 0.5 cm in length. A connective piece 218 is also shown in FIG. 2B that allows the integrated housing and blade assembly to be attached to the tip lumen.

The tonsillectomy tips herein described may provide more precise cutting and coagulation because of the particular suction electrode design. Here not only does the aspiration port suction smoke and fluids from the operative field to improve visualization, but suction and coagulation is capable of being directly and immediately placed on the tonsil bed from which the tonsil tissue has been resected. This is the raw surface where hemostasis is needed most, not on the tonsil itself, which is removed from the body. The active electrode rim also provides a larger surface that could be swept across the tissue to more effectively control bleeding.

Furthermore, use of the tonsil devices described here may result in less thermal injury. As further detailed below in Example 1, the depth of thermal injury was found to be less when the instant tonsil devices were employed in comparison to Bovie needles (0.26 mm vs. 0.77 mm) on tonsil tissue. Thermal injury was decreased by 66% when cut settings were used and by 73% when coagulation settings were used.

The electrical signals (radio frequency in this case) for generating the plasma may be provided by generators and electrical circuits of the kind well known in the art, or by those described in pending co-owned application Ser. Nos. 11/982,734 and 12/136,683, which are incorporated by reference in their entirety. The electrical signals are conventionally applied to the electrode by a conductor(s) extending through the electrosurgical device and not shown here. As previously mentioned, the plasma is formed along the edge of the active electrode by application of the electrical signals to the electrode. To further decrease the heat accumulation and associated collateral tissue damage, low duty cycle waveforms may be used. As well known, duty-cycle refers to the proportion of time that the electrical energy is actually being applied. Low duty-cycle here typically refers to duty-cycles of less than 10% which may be, for instance, 1% or less, or 0.1% or less. In some cases the low duty-cycle refers to the pulse voltage regime that is applied to the active electrode. For instance, a pulsed low duty-cycle signal may include a plurality of pulse bursts that are separated by more than one millisecond (e.g., has a frequency of less than 1 KHz) where each burst is shorter than one millisecond. The burst of pulses may include pulses that are biphasic (e.g., of alternating polarity) and the pulses may have different peak voltages. Again, none of this is limiting. The low duty-cycle is intended to minimize the spread of thermal injury, including tissue charring or burning. However, in some instances the devices described here may employ continuous waveforms or duty cycles of greater than about 50% or greater than about 75%.

Cutting or coagulation is generally obtained by energizing the active electrode with a suitable electrical signal (typically of different frequency, duty-cycle, etc.) for each surgical function. For example, when cutting is desired, the applied signal is an RF (radio frequency) signal having a frequency in the range of 100 KHz to 10 MHz. This energy may be applied in the form of bursts of pulses. Each burst will typically have a duration in the range of 10 microseconds to 1.0 millisecond. The individual pulses in each burst typically each have a duration of 0.1 to 10 microseconds with an interval therebetween of 0.1 to 10 microseconds. The actual pulses are typically square waves and bi-phasic, that is alternating positive and negative amplitudes. Generally the interval between pulses must be shorter than a lifetime of the plasma vapor cavity in order to maintain the cavity and the plasma regime during each pulse burst. In one variation the bursts each are separated by a duration of at least one millisecond. Typically the time between the pulse bursts is sufficient so that the duty-cycle is relatively low as explained above. This minimizes the undesirable heating effects. Coagulation may be achieved in the same manner, but by increasing output power of the device.

The generator associated with the electrosurgical devices may also allow varying degrees of cutting and coagulation. For example, in addition to a default power setting when the device is turned on, other settings to which the device could be adjusted are provided. This would provide in some instances higher hemostasis when cutting.

The electrosurgical devices described here are intended for single use, and can be employed with tonsillectomy, adenoidectomy, or combined procedures. In use, the tonsils and/or adenoids are accessed and a pulsed electrical signal applied to the active electrode of the interchangeable tip to form a plasma. In some variations, the active electrode is a wire electrode. The tissue is then cut or coagulated with the plasma. Suction may or may not be used when cutting or coagulating. In some instances, suction is applied simultaneously with proximal movement (pulling) of the device to suction cut the tissue. In other instances, suction is applied through the active electrode, as described above.

The electrosurgical devices described here may also be useful in "dry field" surgical procedures where there is no electrically conductive fluid added to the surgical field to, for example, aid conduction of energy between the active and return electrodes and/or to provide a cooling effect to the electrodes. When a dry field approach is employed, energy is typically transmitted only by the portion(s) of the active electrode that contacts tissue. In this instance the energy can be selectively provided to the areas in which it is desired. The application of suction to the tissue may further remove body fluids that would be naturally present in the field to further facilitate tissue contact.

Contrastingly, in a wet field (e.g., when the active and/or return electrodes are immersed or submerged in an electrically conductive fluid provided from outside the body), all parts of the active electrode that are in contact with the electrically conductive fluid provide energy. As a result, more energy than required is generally transmitted to the tissue, and less precisely.

Moreover it has been found that a concave blade does not operate well in a wet field (conductive medium) because components of the blade's electric field directed in opposite directions cancel each other. This does not occur in a dry field since current (energy) only flows to the tissue from that part of the blade in direct contact with the tissue. Hence a dry field approach is advantageous here, so the use of aspiration as described here is beneficial to create the dry field. Further, the suction (aspiration) here directed from the center of the blade pulls the tissue into the aspiration port thereby further decreasing the width of the tissue touching the blade and rendering the field even drier, thereby further improving the accuracy of current flow and the electric field effects described above.

The interchangeable tip may be exchanged for another at any time during the procedure. Thus, it may be useful to provide the suction handle and interchangeable tips with blade assemblies in a kit. Given that the device is intended for single use, one or more suction handles could be packaged with one or more interchangeable tips with blade assemblies. The interchangeable tips could be of the same type, e.g., all adenoidectomy tips or all tonsillectomy tips, or a mixture of the two types. In other instances, the kits may include a plurality of interchangeable tips without the suction handle. The interchangeable tips and suction handles may also be individually packaged.

The kits will also generally contain instructions for use. The instructions may include directions on how to start, operate, and shut down the device, as well as directions on how to adjust power level settings. Steps for changing one interchangeable tip to another, e.g., an adenoidectomy tip for a tonsillectomy tip, may also be provided.

The invention described herein will be further understood by the following non-limiting example.

EXAMPLE 1

Comparative Data on Thermal Injury to Tonsil Tissue

Excised human palatine tonsils were subjected to a series of surgical incisions using conventional "Bovie" needle tips at settings of 30 W Cut and 30 W Coag. Additional incisions were made using the electrosurgical tonsillectomy devices described here ("Tonsil Blade") on settings of Cut 5 (20 W power output) for cutting and Coag 6 (30 W power output) for coagulation. Histology samples were harvested immediately after incision and evaluated for residual thermal injury using microscopy. A comparison of the depth of thermal injury (mm) and percent reduction in thermal injury is provided in Table 1.

TABLE 1

Comparison of Thermal Injury Depth in Tonsil Tissue

|  | Thermal Injury Depth (mm) | |
| --- | --- | --- |
|  | Cut | Coag |
| Tonsil Blade (20 W Cut) (30 W Coag) | 0.26 | 0.26 |
| Bovie (30 W Cut) (30 W Coag) | 0.77 | 0.96 |
| Percent Reduction | 66% | 73% |
| p value | $p < 0.05$ | $p < 0.005$ |

EXAMPLE 2

Comparative Data on Thermal Injury to Adenoid Tissue

Excised porcine adenoid tissue was subjected to a series of incisions using an electrosurgical device comprising the active electrode configuration shown in FIGS. 1A-1G at settings of Cut 9 (power output 40 W at 600 Ohms with 1930 Volts peak to peak maximum) for cutting and Coag 7 (power output 30 W at 1000 Ohms with 3960 Volts peak to peak maximum) for coagulation and Cut 10 (power output 50 W at 600 Ohms with 2110 Volts peak to peak maximum) for cutting and Coag 10 (power output 50 W at 1000 Ohms with 5000 Volts peak to peak maximum) for coagulation. Thermal injury from these incisions was compared to thermal injury resulting from an electrosurgical device using the wire electrode and housing design of FIGS. 3 and 4A-4B at the same settings. Histology samples were harvested immediately after incision and evaluated for residual thermal injury using microscopy. A comparison of the depth of thermal injury (mm) is shown in Table 2.

TABLE 2

Comparison of Thermal Injury Depth in Adenoid Tissue

| Settings | Electrode of FIGS. 1A-1G | Wire Electrode |
| --- | --- | --- |
| Cut 9 | 0.45 | 0.32 |
| Coag 7 | 0.48 | 0.31 |
| Cut 10 | 0.72 | 0.26 |
| Coag 10 | 0.52 | 0.32 |

What is claimed is:

1. An electrosurgical device comprising:
a) an elongate body having a proximal end, a distal end, and defining a lumen for applying aspiration extending therethrough;
b) a tip having a proximal end, a distal end, and defining a tip lumen fluidly connected to the aspiration lumen at the distal end of the elongate body;
c) a housing secured to the distal end of the tip and defining an aperture fluidly connected to the tip lumen; and
d) an electrode assembly in the housing and comprising an active electrode, wherein the electrode assembly or a portion thereof defines an aspiration port communicating with the aperture in the housing.

2. The electrosurgical device of claim 1, wherein the active electrode is a wire.

3. The electrosurgical device of claim 2, wherein the wire has a diameter in the range of about 0.0125 mm to about 0.5 mm.

4. The electrosurgical device of claim 3, wherein the wire has a diameter of about 0.2 mm.

5. A method for resecting tissue using the device of claim 1, the method comprising the acts of:
   a) applying a pulsed electrical signal to the electrode to form a plasma thereon; and
   b) cutting or coagulating the tissue with the plasma.

6. The method of claim 5, further comprising the act of applying suction to the tissue through the aspiration port.

7. The method of claim 6, wherein the suction is applied during proximal movement of the electrode to suction cut the tissue.

8. The device of claim 1, wherein a return electrode associated with the active electrode is located remote from the active electrode.

9. The device of claim 1, wherein the tip is malleable.

10. The device of claim 1, wherein the active electrode is partly covered with an electric insulating layer, with an exposed portion.

11. The device of claim 1, wherein the active electrode has a cutting edge and an adjacent planar surface adapted to coagulate tissue.

12. The device of claim 1, further comprising a plurality of arms securing the active electrode to the housing, each arm defining a bend having an angle in the range of 110° to 140°.

13. The device of claim 11, wherein the active electrode cutting edge includes a leading edge portion extending from a remainder of the cutting edge by a distance in the range of 0.2 mm to 2.0 mm.

14. The device of claim 11, wherein the cutting edge and aperture together define the aspiration port.

15. An electrosurgical device comprising:
   a) an elongate body having a proximal end, a distal end, and defining a lumen for applying aspiration extending therethrough;
   b) a tip having a proximal end, a distal end, and defining a tip lumen fluidly connected to the aspiration lumen at the distal end of the elongate body;
   c) a housing secured to the distal end of the tip and defining an aperture fluidly connected to the tip lumen;
   d) an electrode assembly in the housing and comprising an active electrode, wherein the electrode assembly or a portion thereof defines an aspiration port communicating with the aperture in the housing,
   wherein the tip is malleable, and
   wherein the tip includes a plurality of bendable wires extending from the proximal end to the distal end of the tip, whereby the tip is malleably bent and rotated around a longitudinal axis of the elongate body.

16. An electrosurgical device comprising:
   a) an elongate body having a proximal end, a distal end, and defining a lumen for applying aspiration extending therethrough;
   b) a tip having a proximal end, a distal end, and defining a tip lumen fluidly connected to the aspiration lumen at the distal end of the elongate body;
   c) a housing secured to the distal end of the tip and defining an aperture fluidly connected to the tip lumen;
   d) an electrode assembly in the housing and comprising an active electrode, wherein the electrode assembly or a portion thereof defines an aspiration port communicating with the aperture in the housing, and
   wherein the active electrode defines a substantially triangular central opening that is the aspiration port.

17. The device of claim 16, wherein a rim of the active electrode surrounding the central opening has a thickness in the range of 0.5 mm to 3.0 mm and is partially covered with an electric insulating layer, with a part of an outer edge and an inner edge of the rim being exposed.

18. The device of claim 16, wherein the active electrode has a length and width of about 4 mm.

19. The device of claim 16, wherein the active electrode curves at an angle of about 30°, thereby to conform to curvature of a human tonsil.

20. The device of claim 16, wherein the housing tapers towards its distal end at the electrode assembly, wherein the housing covers the aspiration port on one side of the active electrode and only partly covers the aspiration port on an opposing side of the active electrode.

21. The device of claim 16, wherein the aspiration port is about 1.7 mm wide and about 5 mm long.

22. A method for resecting tissue, comprising the acts of:
   moving an electrode relative to the tissue;
   applying a pulsed electrical signal to the electrode to form a plasma thereon;
   cutting or coagulating the tissue with the plasma;
   wherein the electrode is mounted to a housing defining an aperture which communicates with an aspiration port at the electrode; and
   applying suction to the aspiration port via the aperture, thereby to suction the cut or coagulated tissue, while moving the electrode relative to the tissue.

* * * * *